US 11,523,804 B2

(12) United States Patent
Motoki et al.

(10) Patent No.: US 11,523,804 B2
(45) Date of Patent: Dec. 13, 2022

(54) ULTRASONIC DIAGNOSIS DEVICE AND TEMPERATURE MANAGEMENT METHOD

(71) Applicant: Hitachi, Ltd., Tokyo (JP)

(72) Inventors: Kazuya Motoki, Tokyo (JP); Toru Watanabe, Tokyo (JP); Gen Shiina, Tokyo (JP); Kazuhiro Kobayashi, Tokyo (JP)

(73) Assignee: FUJIFILM HEALTHCARE CORPORATION, Kashiwa (JP)

( * ) Notice: Subject to any disclaimer, the term of this patent is extended or adjusted under 35 U.S.C. 154(b) by 0 days.

(21) Appl. No.: 16/628,252

(22) PCT Filed: Jun. 8, 2018

(86) PCT No.: PCT/JP2018/021968
§ 371 (c)(1),
(2) Date: Jan. 2, 2020

(87) PCT Pub. No.: WO2019/017107
PCT Pub. Date: Jan. 24, 2019

(65) Prior Publication Data
US 2020/0170625 A1     Jun. 4, 2020

(30) Foreign Application Priority Data
Jul. 19, 2017 (JP) ............... JP2017-139601

(51) Int. Cl.
*A61B 8/00*     (2006.01)
*A61B 8/15*     (2006.01)
*G01K 11/26*    (2006.01)

(52) U.S. Cl.
CPC ............ *A61B 8/546* (2013.01); *A61B 8/15* (2013.01); *A61B 8/4444* (2013.01); *A61B 8/466* (2013.01);
(Continued)

(58) Field of Classification Search
CPC ....... A61B 8/546; A61B 8/4444; G01K 11/26
See application file for complete search history.

(56) References Cited

U.S. PATENT DOCUMENTS 7,993,056 B2 *  8/2011  Amemiya ............. G01S 15/899
                                                      374/117
2009/0213897 A1   8/2009  Amemiya
(Continued)

FOREIGN PATENT DOCUMENTS

JP     H07-135731 A    5/1995
JP     2009-005994 A   1/2009
(Continued)

OTHER PUBLICATIONS

Saunders, O., S. Clift, and F. Duck. "Ultrasound transducer self heating: development of 3-D finite-element models." Journal of Physics: conference series. vol. 1. No. 1. IOP Publishing, 2004.*
(Continued)

*Primary Examiner* — Ashley K Buran
*Assistant Examiner* — Sean V Blinder
(74) *Attorney, Agent, or Firm* — Foley & Lardner LLP

(57) ABSTRACT

In order to estimate a temperature of a transmission-reception wavefront of a probe head, a first computing unit and a second computing unit are provided. The first computing unit estimates a temperature TA of the transmission-reception wavefront according to a basic function based on an internal temperature T1, an ambient temperature T2, power consumption Ptotal (=Pic+Ptd), and any other parameter. The basic function is a linear function. The second computing unit estimates a temperature TB of the transmission-reception wavefront according to an auxiliary function based on a previously estimated temperature Tpre, an internal
(Continued)

temperature difference ΔT1, and any other, parameter. A selection unit selects any of the temperatures TA and TB depending on situations.

7 Claims, 7 Drawing Sheets

(52) U.S. Cl.
CPC .............. *A61B 8/54* (2013.01); *A61B 8/56* (2013.01); *G01K 11/26* (2013.01)

(56) References Cited

U.S. PATENT DOCUMENTS

| | | | |
|---|---|---|---|
| 2010/0331702 A1* | 12/2010 | Hongou | A61B 8/546 600/459 |
| 2011/0298528 A1 | 12/2011 | Endo | |
| 2012/0029353 A1* | 2/2012 | Slayton | A61B 8/4254 600/439 |
| 2015/0164483 A1 | 6/2015 | Miyajima | |
| 2017/0007213 A1* | 1/2017 | Motoki | G01S 7/52079 |
| 2018/0278822 A1* | 9/2018 | Takahashi | H04N 5/243 |

FOREIGN PATENT DOCUMENTS

| | | | | |
|---|---|---|---|---|
| JP | 2010-000137 A | | 1/2010 | |
| JP | 2010000137 A | * | 1/2010 | |
| JP | 2011-036095 A | | 2/2011 | |
| JP | 2011-258623 A | | 12/2011 | |
| JP | 2014-097372 A | | 5/2014 | |
| JP | 5771293 B2 | | 8/2015 | |
| WO | WO-2015/111265 A1 | | 7/2015 | |
| WO | WO-2015111265 A1 | * | 7/2015 | ............. A61B 8/445 |

OTHER PUBLICATIONS

International Preliminary Report on Patentability issued in corresponding International Application No. PCT/JP2018/021968 dated Jan. 30, 2020, including Forms PCT/IB/326 and PCT/IB/338.
International Search Report with English translation and Written Opinion issued in corresponding application No. PCT/JP2018/021968 dated Aug. 7, 2018.

* cited by examiner

ULTRASONIC DIAGNOSIS DEVICE AND TEMPERATURE MANAGEMENT METHOD

TECHNICAL FIELD

The present invention relates to an ultrasonic diagnostic apparatus, and more specifically to the management of the temperature of transmission and reception faces of an ultrasound probe.

BACKGROUND ART

The ultrasonic diagnostic apparatus is a medical apparatus that forms ultrasound images using ultrasonic transmission and reception waves to and from a living body. The ultrasonic diagnostic apparatus is chiefly configured of an ultrasound probe and an apparatus main body. The ultrasound probe is formed of a probe head, a cable, and a connector. The probe head has an ultrasonic transducer. As the ultrasonic transducer, a transducer element array formed of a plurality of transducer elements is generally provided. In addition to a 1D transducer element array having a plurality of transducer elements linearly arrayed, a transducer element array formed of a plurality of transducer elements that are two-dimensionally arrayed is also used. Ultrasonic wave beams are two-dimensionally scanned by the 2D transducer element array, and hence a three-dimensional data capture space is formed. A three-dimensional image, tomographic image, and any other image is formed based on volume data acquired from the inside of the three-dimensional data capture space. Note that the three-dimensional image is an image that biological tissue is three-dimensionally or three-dimensionally expressed, and is physically a two-dimensional image. A probe that forms a three-dimensional data capture space using a 2D transducer element array is referred to as an electronic 3D probe.

Generally, in the probe head of the electronic 3D probe, an electronic circuit for channel reduction (a sub-beam former, for example) is provided. Both of the ultrasonic transducer and the electronic circuit work as heat sources, and the heat caused by the ultrasonic transducer and the electronic circuit increases the temperature of the transmission-reception wavefront of the probe head (the acoustic lens or the surface of the protective layer in contact with the living body surface). From the viewpoint of the safety of the living body, the operation of the ultrasonic diagnostic apparatus (more specifically, the transmission operation) is controlled such that the temperature of the transmission-reception wavefront does not exceed the upper limit of the temperature.

Patent Literature 1 discloses an ultrasonic diagnostic apparatus having an ultrasound probe that is inserted into the inside of the body cavity. In the probe head of the ultrasound probe, a 2D transducer element array, an electronic circuit, a temperature sensor, and any other component are provided. The temperature of the transmission-reception wavefront is estimated from the temperature detected by the temperature sensor and the power consumption at the ultrasound probe.

Note that Patent Literature 2 discloses an ultrasonic diagnostic apparatus having a temperature sensor provided in a probe head and an external temperature sensor provided outside the probe. The temperature of the transmission-reception wavefront is estimated based on two temperatures detected by these two temperature sensors. In the ultrasound probe described in Patent Literature 2, the heat source is the ultrasonic transducer alone, and no electronic circuit is provided there. Patent Literature 3 discloses the provision of an ambient temperature sensor is provided in a connector box in the ultrasound probe.

CITATION LIST

Patent Literature

Patent Literature 1: Japanese Patent No. 5,771,293
Patent Literature 2: Japanese Unexamined Patent Application Publication No. 2009-5994
Patent Literature 3: Japanese Unexamined Patent Application Publication No. 2010-137

SUMMARY OF INVENTION

Technical Problem

From the viewpoint of the safety of the living body, the temperature of the transmission-reception wavefront in the ultrasound probe has to be unerringly managed. The temperature of the transmission-reception wavefront is dependent on various factors (heat generation in the ultrasonic transducer, heat generation in the electronic circuit, the heat dissipation structure, the living body temperature, the ambient temperature, and any other factor). Estimating the temperature of the transmission-reception wavefront using a single temperature estimation function (a basic function) easily causes estimation errors in a transition period in which the state greatly changes specifically. Patent Literatures 1 to 3 describe no combination use of a plurality of temperature estimation functions.

An object of the present invention is to improve the estimation accuracy of the temperature of the transmission-reception wavefront in an ultrasound probe, and to unerringly manage the temperature of the transmission-reception wavefront. Alternatively, an object of the present invention is to enable the estimation of the temperature of the transmission-reception wavefront at a certain accuracy in a normal period in which the temperature can be estimated by the basic function as well as in the transition period in which it is difficult to estimate the temperature using the basic function. Alternatively, an object of the present invention is to enable the estimation of the temperature of the transmission-reception wavefront also in consideration of the influence of the ambient temperature.

Solution to Problem

An ultrasonic diagnostic apparatus according to the embodiment includes: a probe head including an ultrasonic transducer, an electronic circuit electrically connected to the ultrasonic transducer, an internal temperature sensor configured to detect an internal temperature, and a transmission-reception wavefront; and an estimator configured to estimate a temperature of the transmission-reception wavefront based on a transmission-reception condition and the internal temperature, the estimator being configured to estimate a temperature of the transmission-reception wavefront based on a function group including a basic function that is a temperature estimation function for a normal period and an auxiliary function that is a temperature estimation function for a transition period in which the basic function is not held.

A temperature management method according to the embodiment includes the steps of: estimating a temperature of a transmission-reception wavefront on a probe head having an ultrasonic transducer, an electronic circuit, and the transmission-reception wavefront; and controlling transmission and reception by the estimated temperature. The estimating step includes the steps of: computing a temperature of the transmission-reception wavefront as a first temperature based on a basic function that is a temperature estimation function in a stable period in which a temperature of the transmission-reception wavefront; computing a temperature of the transmission-reception wavefront as a second temperature based on an auxiliary function that is a temperature estimation function for a transition period; and selecting the first temperature or the second temperature as an estimated temperature.

DESCRIPTION OF EMBODIMENTS

Figure 1:
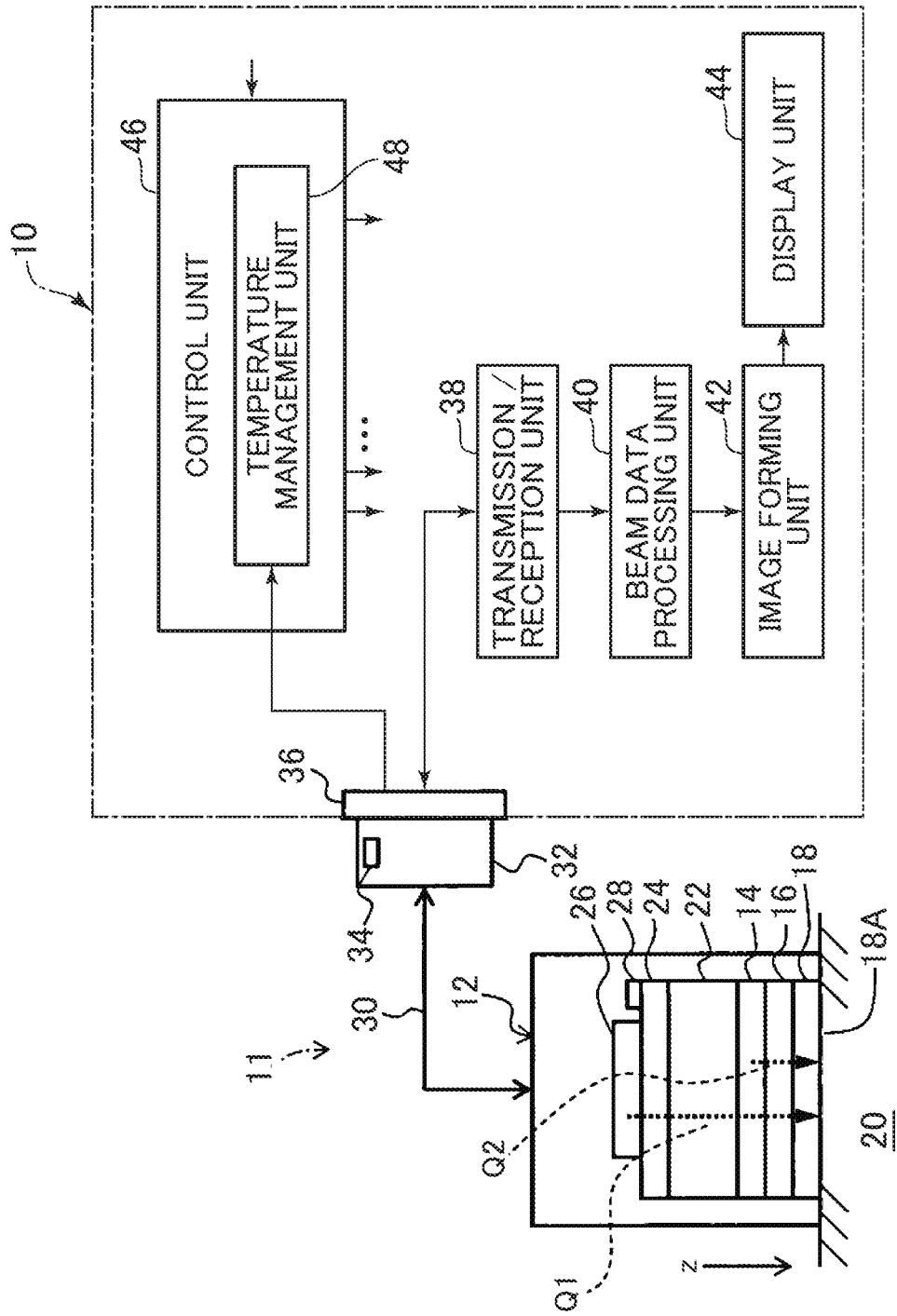
FIG. 1 is a block diagram showing the configuration of an ultrasonic diagnostic apparatus according to an embodiment.

In the following, an embodiment will be described with reference to the drawings.

(1) Summary of the Embodiment

An ultrasonic diagnostic apparatus according to the embodiment includes a probe head and an estimator. The probe head includes an ultrasonic transducer, an electronic circuit electrically connected to the ultrasonic transducer, an internal temperature sensor configured to detect an internal temperature, and a transmission-reception wavefront. The estimator is configured to estimate a temperature of the transmission-reception wavefront based on a transmission-reception condition and the internal temperature. More specifically, the estimator is configured to estimate a temperature of the transmission-reception wavefront based on a function group including a basic function that is a temperature estimation function for a normal period and an auxiliary function that is a temperature estimation function for a transition period in which the basic function is not held.

According to the configuration, the temperature of the transmission-reception wavefront is estimated using the function group including the basic function for the normal period (a stable change period) and the auxiliary function for the transition period (a sudden change period). In the transition period, the temperature can be estimated using the auxiliary function, and hence estimation accuracy can be enhanced, compared with the case in which the temperature is estimated using a single basic function alone. A plurality of the auxiliary function may be used.

In the ultrasonic diagnostic apparatus according to in the embodiment, a selector is provided, the selector being configured to compute a first temperature according to the basic function and a second temperature according to the auxiliary function in a parallel manner, select any of the first temperature and the second temperature, and output the selected temperature as an estimated temperature. In the embodiment, the selector selects any of the first temperature and the second temperature based on the internal temperature, and on a comparison result of the first temperature with the second temperature.

The ultrasonic diagnostic apparatus according to the embodiment further includes an ambient temperature sensor configured to detect an ambient temperature. The estimating unit estimates a temperature of the transmission-reception wavefront further based on the ambient temperature. According to the configuration, the estimation accuracy of the temperature of the transmission-reception wavefront can be further enhanced. More specifically, in the case in which an ultrasound probe that contacts the body surface is used, it is highly necessary to take into consideration of the ambient temperature in the estimation of the temperature.

In the embodiment, the basic function temperature of the transmission-reception wavefront is a linear expression that estimates a temperature of the transmission-reception wavefront based on power consumption that is based on the transmission-reception condition, the internal temperature, and the ambient temperature. That is, the basic equation is described in the form of the linear expression.

In the embodiment, the auxiliary function is a recurrence formula that estimates a temperature of the transmission-reception wavefront based on a previously estimated temperature and a difference between an internal temperature detected at a present time and a previously detected internal temperature. The ultrasonic transducer is located near the transmission-reception wavefront, and it is recognized that the temperature of the transmission-reception wavefront quickly responds to heat generation in the ultrasonic transducer, and hence the power consumption of the ultrasonic transducer is desirably a parameter in the auxiliary function.

In the embodiment, a connector is connected to the probe head through a cable; the connector includes an outer case that is a case, an electronic circuit board, and an inner case provided in the outer case, the inner case that is a shield case surrounding the electronic circuit board; and between the outer case and the inner case, the ambient temperature sensor is provided.

According to the configuration, the temperature sensor that detects the ambient temperature is incorporated in the ultrasound probe itself that is a target for temperature management. Additionally, the connector is apart from the probe head, and hence the sneaking of heat from the probe head can be ignored. When the ambient temperature sensor is disposed between the outer case the inner case, the ambient temperature sensor can be physically protected, and simultaneously, the influence of the heat can be suppressed even though the electronic circuit board slightly generates heat (or even though heat is conducted from the apparatus main body).

A temperature management method according to the embodiment includes the steps of: estimating a temperature of a transmission-reception wavefront on a probe head having an ultrasonic transducer, an electronic circuit, and the transmission-reception wavefront; and controlling transmission and reception by the estimated temperature. The estimating step includes the steps of: computing a temperature of the transmission-reception wavefront as a first temperature based on a basic function that is a temperature estimation function in a stable period in which a temperature of the transmission-reception wavefront; computing a temperature of the transmission-reception wavefront as a second temperature based on an auxiliary function that is a temperature estimation function for a transition period; and selecting the first temperature or the second temperature as an estimated temperature.

Based on the direction of change in the power consumption in the probe head and the comparison result of the first temperature with the second temperature, the first temperature or the second temperature may be selected as an estimated temperature.

The method can be implemented as the functions of hardware or the functions of software. In the case of the latter, a program that executes the method is installed on the ultrasonic diagnostic apparatus through a storage medium or via a network.

According to the embodiment, the estimation accuracy of the temperature of the transmission-reception wavefront can be enhanced, compared with the case in which the temperature of the transmission-reception wavefront is estimated based on a single basic function. Thus, the temperature of the transmission-reception wavefront can be unerringly managed, and at the same time, the occurrence of operation restriction more than necessary due to an excess reservation of a margin for safety can be avoided. Alternatively, according to the embodiment, in addition to the normal period in which the temperature can be estimated by the basic function, also in the transition period in which it is difficult to estimate the temperature using the basic function, the temperature of the transmission-reception wavefront can be estimated at a certain accuracy. Alternatively, the temperature of the surface-reception wavefront can be estimated also in consideration of the influence of the ambient temperature.

(2) Detail of the Embodiment

FIG. 1 shows an ultrasonic diagnostic apparatus according to the embodiment. This ultrasonic diagnostic apparatus is a medical apparatus that transmits and receives ultrasonic waves to and from a living body and forms ultrasound images based on the reception signals thus obtained.

In FIG. 1, the ultrasonic diagnostic apparatus is configured of an apparatus main body 10 and an ultrasound probe 11. The ultrasound probe 11 is formed of a probe head 12, a cable 30, and a connector 32. The connector 32 is detachably connected to a connector 36 on the apparatus main body 10 side.

The probe head 12 functions as an ultrasonic transducer, and a transmission-reception wavefront 18A of the probe head 12 contacts the surface of a living body 20. The probe head 12 has an ultrasonic transducer 14. In the embodiment, the ultrasonic transducer 14 is formed of a plurality of transducer elements two-dimensionally arrayed in an x-direction and in a Y-direction orthogonal to a Z-direction, shown in the drawing, i.e., the ultrasonic transducer 14 is formed of a transducer element array. On the front side (the living body side) of the ultrasonic transducer 14, a matching layer 16 is provided, and further on the front side of the matching layer 16, a protective layer 18 is provided. The matching layer 16 is configured of a matching element array formed of a plurality of matching elements. A plurality of the matching layer may be stacked in the Z-direction. The surface of the protective layer 18 is the transmission-reception wavefront 18A. The transmission-reception wavefront 18A is the face that contacts the living body 20. From the viewpoint of the safety of the living body, the temperature of the transmission-reception wavefront 18A has to be managed. For example, it is requested to control transmission and reception such that the temperature of the transmission-reception wavefront 18A does not exceed a predetermined temperature (e.g. 43 degrees).

On the rear side (the non-living body side) of the ultrasonic transducer 14, a backing 22 is provided. The backing 22 has a built-in lead array formed of a plurality of leads that is two-dimensionally arrayed. On the rear side of the backing 22, an IC (integrated circuit) 26 is provided, which is a relay substrate 24 and an electronic circuit. The IC 26 has a channel reduction function, i.e., a sub-beam forming function. The terminal group of the IC 26 is electrically connected to the transducer element array through the relay substrate 24 and the lead array. On the back surface of the relay substrate 24, a temperature sensor 28 is provided. The temperature sensor 28 is configured of a thermistor, for example. The temperature sensor 28 detects the internal temperature of the probe head 12, and specifically detects the internal temperature near the position of the IC 26. A plurality of temperature sensors may be disposed in the inside of the probe head 12. Instead of the body surface contacts type ultrasound probe, a body cavity insertion type ultrasound probe may be used. A 1D ultrasound probe may be used. A wireless ultrasound probe may be used.

In the probe head 12, the IC 26 and the ultrasonic transducer 14 are heat sources. Heat conducted from the IC 26 to the transmission-reception wavefront 18A is denoted by Q1 in FIG. 1. Heat conducted from the ultrasonic transducer 14 to the transmission-reception wavefront 18A is denoted by Q2 in FIG. 1. Although in the transition period, such as immediately after the start of transmission, the temperature of the living body 20 or the ambient temperature is sometimes higher than the temperature of the ultrasonic transducer 14 or the IC 26.

Between the probe head 12 and the connector 32, the cable 30 is provided. The cable 30 has a hundred and a few tens of signal lines, for example. In the embodiment, the connector 32 has a temperature sensor 34 that measures the ambient temperature. The temperature sensor 34 is configured of a thermistor, for example. The ultrasonic diagnostic apparatus according to the embodiment has a function that estimates the temperature of the transmission-reception wavefront 18A based on diagnostic modes (a B-mode, a CW-mode, and any other mode), transmission-reception conditions involved in power consumption, the internal temperature, the ambient temperature, and any other condition, as described later.

The apparatus main body 10 will be described. The transmission-reception unit 38 is an electronic circuit that functions as a main beam former. More specifically, the transmission-reception unit 38 outputs a plurality of transmission signals subjected to delay processing in transmission to the IC 26. The IC 26 generates a plurality of transmission signals given to a plurality of transducer elements, which is a few hundreds or a few thousands of transducer elements, based on the plurality of transmission signals. In reception, a plurality of reception signals from the plurality of transducer elements is subjected to delay addition processing at the IC 26, and a plurality of processed reception signals is sent to the transmission-reception unit 38. The transmission-reception unit 38 further applies delay addition processing to the plurality of reception signals, and thus outputs beam data corresponding to a reception beam. For example, a piece of reception frame data is generated per ultrasonic wave beam scanning in the x-direction at a time. A piece of reception frame data is configured of a plurality of pieces of beam data. The individual pieces of beam data is configured of a plurality of pieces of echo data arranged in the depth direction.

A beam data processing unit 40 is an electronic circuit that sequentially processes beam data. Examples of processing include detection processing, logarithmic transformation processing, correlation processing, and any other processing. An image forming unit 42 is configured of an electronic circuit, and more specifically, the image forming unit 42 is configured of a digital scan converter (DSC). The image forming unit 42 generates a display frame data string based on a reception frame data string. In the generation, processes, such as coordinate transformation, pixel interpolation, and rate transformation, are executed. The display frame data string is configured of a plurality of pieces of display frame data arranged on a time base, and forms a B-mode tomographic image as a time-varying image, for example. A three-dimensional image, and a Doppler waveform image, for example, may be formed. On the display screen of a display unit 44, an ultrasound image is displayed. The display unit 44 is configured of an organic EL device and an LCD, for example.

A control unit 46 is configured of a CPU that executes programs. The control unit 46 may be configured of a plurality of processors. The control unit 46 controls the individual components shown in FIG. 1, and more specifically, the control unit 46 includes a function that manages the temperature of the transmission-reception wavefront. In FIG. 1, the function is expressed as a temperature management unit 48. To the temperature management unit 48, information including probe types, diagnostic modes, transmission-reception conditions, the internal temperature, and the ambient temperature, for example, is given. Based on these pieces of information, the temperature management unit 48 estimates the temperature of the transmission-reception wavefront, or controls the operation of the apparatus according to the estimated temperature. For example, in the case in which the estimated temperature reaches a limiting value or a threshold, the temperature management unit 48 executes control that forcedly stops transmission and reception. The estimated temperature is displayed as a numerical value, for example, on the screen of the display unit 44 according to the situations. To the control unit 46, an operation panel, not shown in the drawing, is connected. The operation panel is an input device having a track ball, a switch, a knob, and a keyboard, for example.

Figure 2:
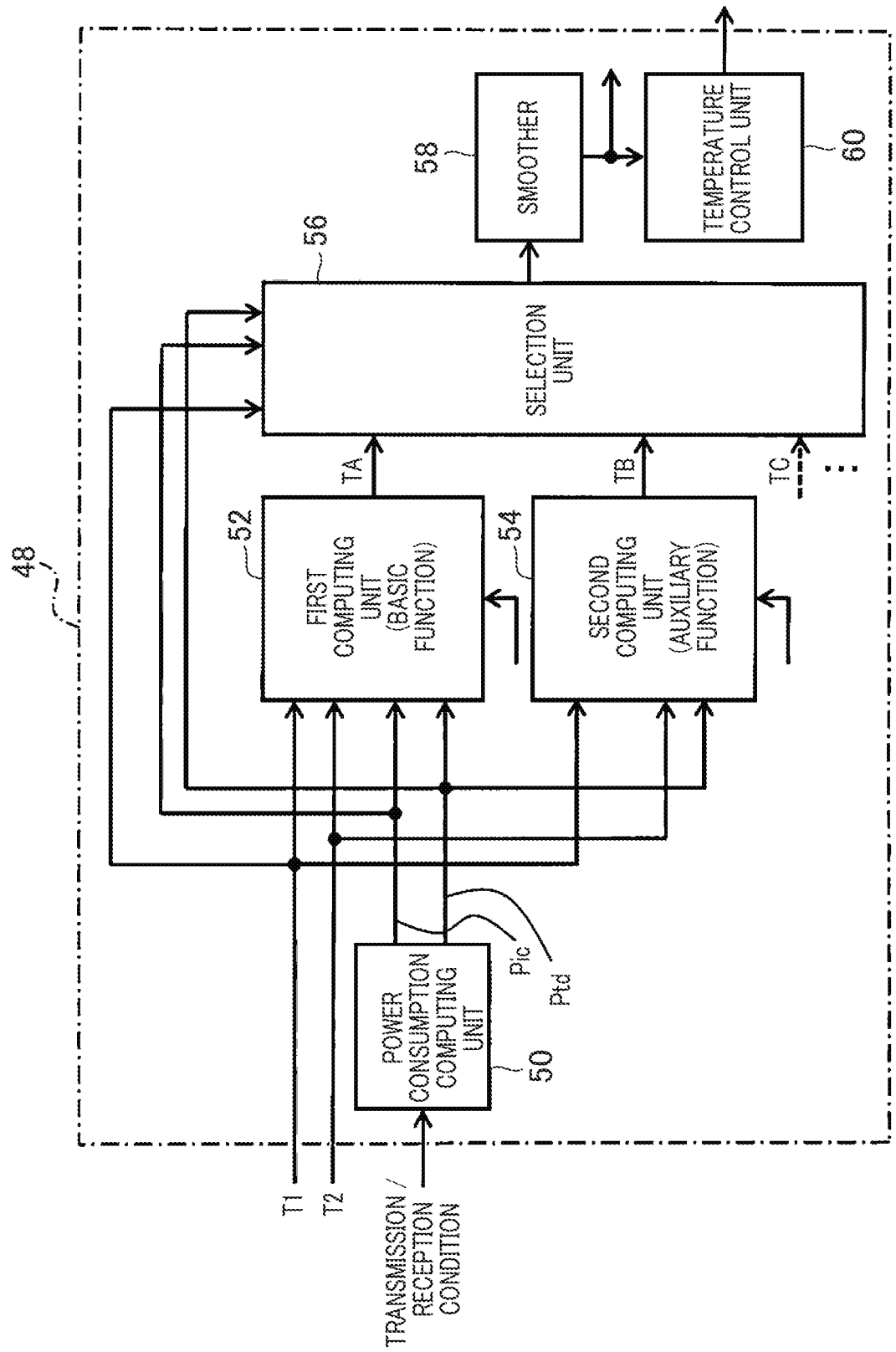
FIG. 2 is a block diagram showing an exemplary configuration of a temperature management unit shown in FIG. 1.

FIG. 2 shows an exemplary configuration of the temperature management unit 48 shown in FIG. 1 as a block diagram. The individual blocks actually correspond to programs. However, the individual block may be configured of processors or devices.

A power consumption computing unit 50 is a module that computes power consumption based on the diagnostic mode and the transmission-reception conditions. Examples of the transmission-reception conditions include a transmission voltage, transmit frequency, wave number, PRT (pulse cycle period), transmission channel number (the number of elements configuring transmission openings), transmission weight function, reception channel number, reception weight function, and any other condition. In the embodiment, both of the power consumption Pic of the IC and the power consumption Ptd of the ultrasonic transducer are computed. The observable parameter viewed from the apparatus main body is the power consumption of the entire ultrasound probe, and the component that the apparatus main body first sees is the IC, and hence the power consumption viewed from the apparatus main body is the power consumption Pic of the IC. With reference to the power consumption Pic, the power consumption Ptd of the ultrasonic transducer is estimated as internal division power consumption. Although this is the convenience for computing, a configuration may be provided in which the power consumption of the IC alone is determined and this is included in the basis of the estimation of the temperature. The power consumption may be individually determined according to another computing criterion. Power consumption Ptotal, described later, is the addition of the power consumption Pic and the power consumption Ptd, for convenience.

Compared with the ultrasound probe inserted into the inside of the body cavity, in the case of the ultrasound probe that contacts the body surface, the power consumption of the ultrasonic transducer (heat generation) is considerably large, and it is desired to estimate the temperature of the transmission-reception wavefront in consideration of the power consumption of the ultrasonic transducer.

A first computing unit 52 estimates the temperature of the transmission-reception wavefront according to the basic function (in order to distinguish between two temperatures estimated by two computing units 52 and 54, the temperature estimated by the first computing unit 52 is denoted as TA, and the temperature computed by the second computing unit 54 is denoted as TB). The basic function is a function that estimates the temperature in the normal period (a stable change period). From the results of experiments and studies, a linear expression shown below is found as a basic function.

$$TA = \alpha \times T1 + C1 + C2 + C3 \qquad (1)$$

In Equation (1) above, T1 is the detected internal temperature (in the present specification, all the temperatures are expressed by Celsius). α is a slope coefficient, and a constant value, 0.6, 0.7, or 0.8, for example, is determined corresponding to the ultrasound probe. The term (C1+C2+C3) defines an intercept (offset) as a whole. For more detail, C1 is determined by the multiplication of the power consumption Ptotal (=Pic+Ptd) by a predetermined coefficient. C2 is determined by the multiplication of an ambient temperature Tenv by a predetermined coefficient. C3 is a constant for adjustment. Equation (1) above expresses that the temperature TA of the transmission-reception wavefront is proportional to the internal temperature T1 and that the power consumption Ptotal and the ambient temperature T2 define the intercept. However, other the other functions may be used as a basic function corresponding to the probe structure. According to Equation (1) above, the temperature TA is computed at a certain time interval (e.g. a one-second interval).

The second computing unit 54 estimates the temperature of the transmission-reception wavefront as the second temperature TB according to an auxiliary function. The auxiliary function is a function that estimates the temperature of the transmission-reception wavefront in the transition period (a period in which the state suddenly changes), i.e., in a period in which the estimation of the temperature by the basic function is not held. From the results of experiments and studies, a recurrence formula shown below is found as an auxiliary function.

$$TB = Tpre + \beta \times \Delta T1 \qquad (2)$$

In Equation (2), Tpre is the temperature (TA or TB) estimated in the previous computing. ΔT1 is the differential value obtained by subtracting, from the internal temperature T1 that is presently detected, an internal temperature T1pre that is previously detected (ΔT1=T1−T1pre). β is a slope coefficient. It is desirable to adaptively vary β corresponding to the diagnostic mode or the apparatus status.

Note that in the start of use of the probe, to Tpre, a temperature determined from the internal temperature T1 and the ambient temperature T2 may be given. To Tpre, a living body temperature my be given. According to Equation (2), the temperature TB is computed at a certain time interval (e.g. a one-second interval). A selection unit 56, described later, operates in synchronization with the operation timing of the first computing unit 52 and the second computing unit 54.

Equation (2) assumes that the temperature Tpre estimated in the previous computing is correct, and on the basis of the assumption, Equation (2) estimates the temperature of the transmission-reception wavefront TB at a present time from the direction of change and the variation of the internal temperature T1, while assuring continuity from the basis.

According to the combination of the basic function and the auxiliary function, although based on a simple estimation of the temperature by the basic function, in the transition period in which estimation is difficult using the basic function, the temperature can be estimated at a certain accuracy. That is, the temperature can be estimated real time under the situations. In the case in which the basic function is used alone, estimated temperature greatly changes when the power consumption is changed, i.e., a problem is prone to cause a large difference between the previously estimated temperature and the temperature estimated at a present time. However, according to the configuration, temporary application of the auxiliary function can avoid the occurrence of such a problem, or that problem can be reduced. Note that the first computing unit 52 and the second computing unit 54 function as estimating units or estimators. The selection unit 56, described below, functions as a selecting unit or a selector.

The selection unit 56 is a module that outputs any of the estimated temperature TA and the temperature TB as an estimated temperature T. In the selection of the estimated temperature T, reference may be made to the internal temperature T1, the power consumption Pic, the power consumption Ptd, the temperature TA, and the temperature TB. In the case in which the comparison result of the temperature TA with the temperature TB satisfies the selection criteria, both of the temperature TA and the temperature TB are concurrently computed prior to selection. The direction of change in the power consumption in the probe head, for example, may be included in the selection criteria.

In the embodiment, the temperatures TA and TB are computed according to the basic function and the auxiliary function. However, a configuration may be provided in which the temperature TC, for example, is further computed according to another function and the computed temperature is added to a selection target.

A smoother 58 is a module that makes reference to a predetermined number (e.g. eight) of the estimated temperatures that are counted from the estimated temperature computed at the present point in time in the past direction and outputs the mean value. Another smoothing method may be adopted.

A temperature control unit 60 performs control in which the temperature control unit 60 displays the estimated temperature T as a numerical value in a normal display mode when the estimated temperature T is a first temperature Tx1 (e.g. 36 degrees) or more and less than a second temperature Tx2 (e.g. 40 degrees), whereas the temperature control unit 60 displays the estimated temperature T as a numerical value in a highlighted display mode when the estimated temperature T is the second temperature Tx2 or more and less than a third temperature Tx3 (e.g. 43 degrees), and simultaneously displays an alarm message. The temperature control unit 60 performs control in which the temperature control unit 60 displays the estimated temperature T at the third temperature Tx3 or more when the estimated temperature T is at the third temperature Tx3 or more, as well as the temperature control unit 60 forcedly stops transmission and reception. Thus, a state for cooldown is formed. After that, in the case in which the estimated temperature T is less than a fourth temperature Tx4 (e.g. 40 degrees), the temperature control unit 60 performs control in which the temperature control unit 60 permits transmission and reception. However, actually, transmission and reception are possible after freeze release operation by an inspector. However, these control contents are merely examples. In the comparison of the thresholds, variations in the temperature or estimation errors may be taken into consideration.

Figure 3:
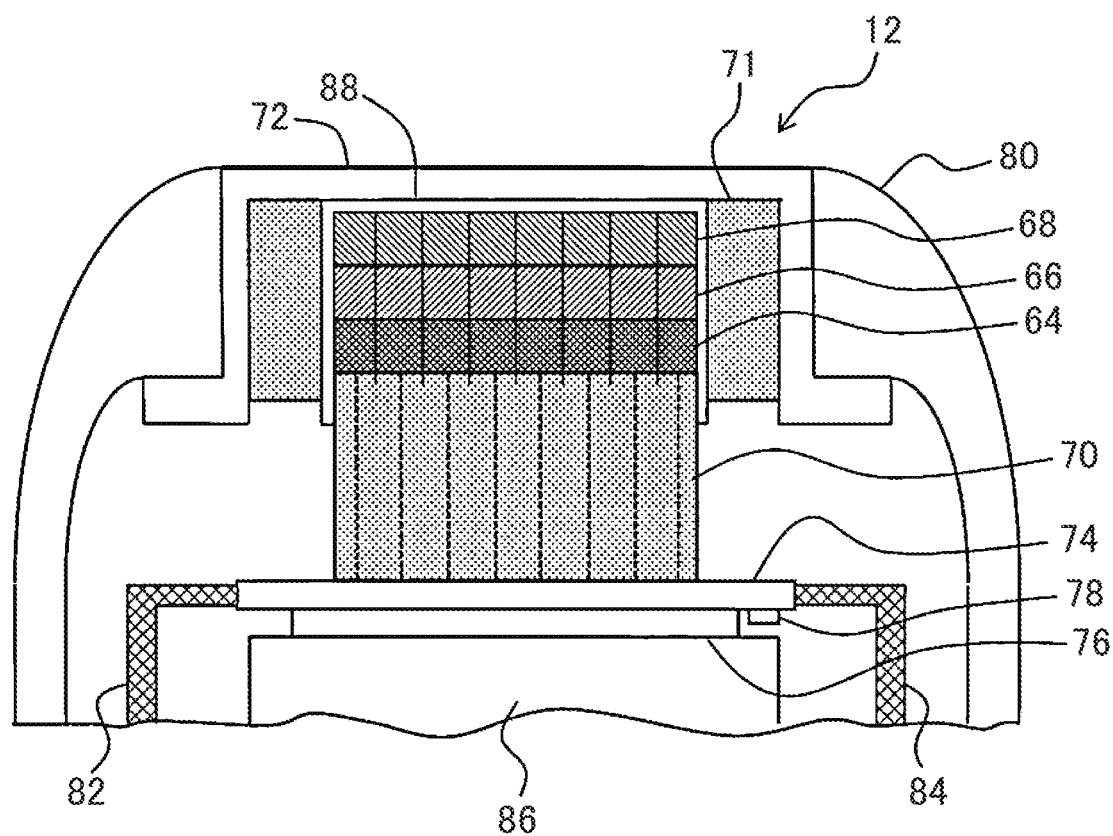
FIG. 3 a cross sectional view of a probe head.

FIG. 3 shows the detailed structure of the probe head 12 shown in FIG. 1. In FIG. 3, the upper direction in the paper surface is the Z-direction (the contact direction). A two-dimensional transducer element array 66 is configured of a piezoelectric material, and is configured of ceramics, such as PZT, and a single crystal, such as PMN-PT, for example. On the front side (the living body side) of the two-dimensional transducer element array 64, a two-dimensional matching element array 68 is provided. Two or more matching layers may be provided there. On the front side of the two-dimensional matching element array 68, a protective layer 72 is provided through a barrier film 88. The protective layer 72 is configured of silicone rubber, for example. The surface (the transmission-reception wavefront) of the protective layer 72 may be curved. On the rear side (the non-living body side) of the two-dimensional transducer element array 66, the two-dimensional hard backing (HB) element array 64 is provided. The individual HB elements function as resonators in the relationship of the corresponding transducer elements. The individual HB elements are configured of a conductive material. The combination body of the HB element and the transducer element corresponds to $\lambda/2$ as a whole ($\lambda$ is a wavelength at the center frequency). On the rear side of the two-dimensional the HB element array 64, a backing (a soft backing) 70 is provided. The backing 70 is configured of a member that attenuates ultrasonic waves emitted to the rear side. In the backing 70, a lead array formed of a plurality of leads is embedded. On the rear side of the backing 70, a relay substrate 74 is provided. The relay substrate 74 is an interposer, and is configured as a multi-layer substrate. To the back surface of the relay substrate 74, an IC 76 that is an electronic circuit is joined. The IC 76 is mounted on the relay substrate 74 by flip chip. The terminal group of the IC 76 is electrically connected to the two-dimensional transducer element array through the relay substrate 74, the lead array, and the two-dimensional the HB element array 64.

On the back surface of the relay substrate 74 and near the IC 76, a temperature sensor 78 that detects the internal temperature T1 is provided. The temperature sensor 78 is configured of a thermistor. On the relay substrate 74, a plurality of temperature sensors may be provided. The temperature sensor 78 may be provided at another place where the thermal conduction conditions are satisfied (e.g. the side surface of the backing 70 or another substrate). To the relay substrate 74, two flexible printed circuits (FPCs) 82 and 84 are connected. The conductive line strings formed on the FPCs 82 and 84 are connected to a plurality of signal lines, not shown in the drawing. To the back surface of the IC 76, a heat dissipation block 86 is joined. A heat dissipation block 86 having a backing effect may be used. Note that the inside of the protective layer 72 and the surrounding around the barrier film 88 is filled with an adhesive 71. A reference sign 80 denotes a resin case. In the configuration above, the temperature sensor 78 detects the internal temperature T1 near the IC 76 as the temperature close to the temperature of the transmission-reception wavefront 18A.

Figure 4:
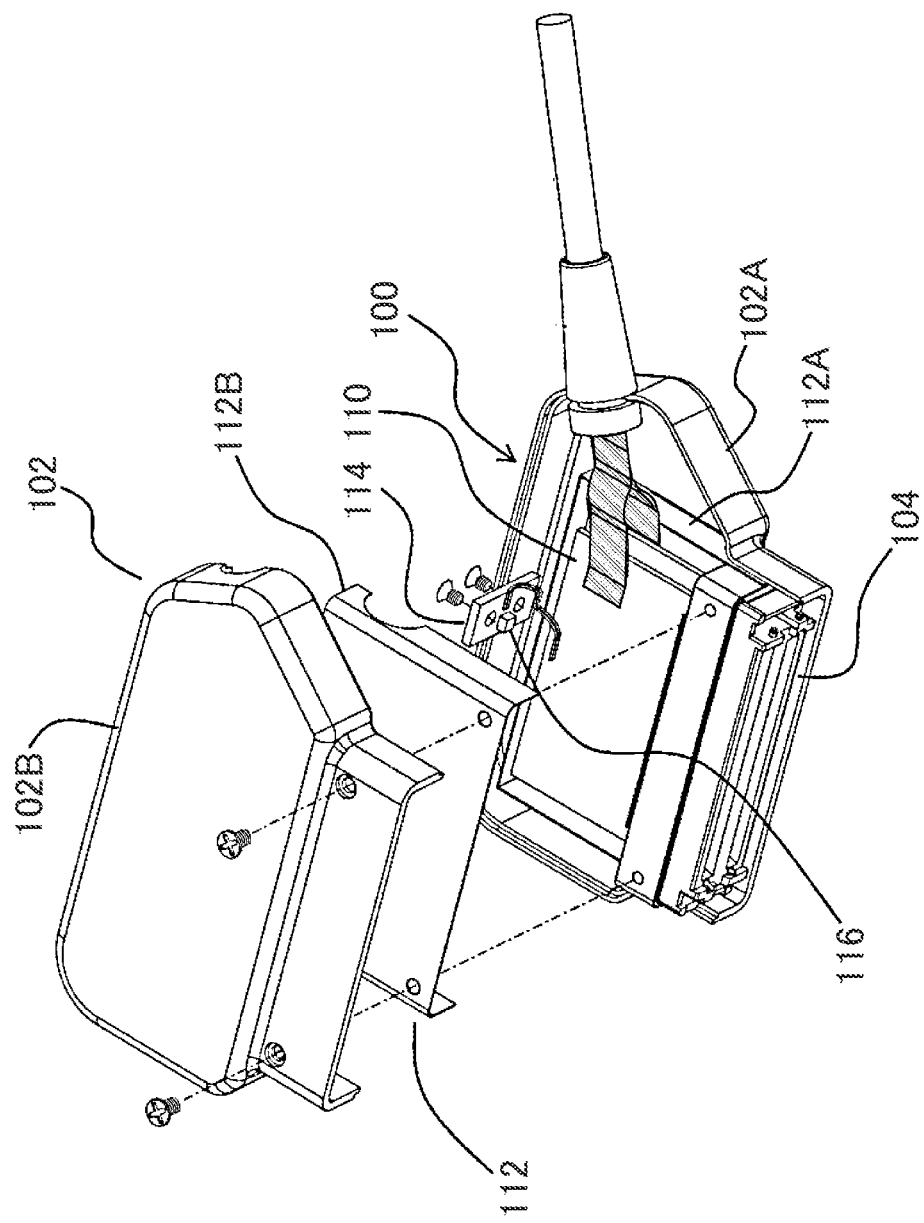
FIG. 4 is an exploded perspective view of a connector.

FIG. 4 shows a connector 100 (see the reference sign 32 in FIG. 1). The outer case 102 is a hollow case made of a resin, and is formed of two half cases 102A and 102B. In the inside of the outer case 102, an inner case 112 made of a metal is provided. The inner case 112 is also formed of two half cases 112A and 112B. In the inside of the inner case 112, a plurality of electronic circuit boards 110 is provided. The inner case 112 is provided such that the plurality of electronic circuit boards 110 is wrapped. The inner case 112 exerts the effect of electromagnetic shielding to the individual electronic circuit boards 110. That is, the inner case 112 is a shield case. The plurality of electronic circuit boards 110 is physically coupled to a connector block 104. The individual electronic circuit boards 110 are mounted with a plurality of electronic components (including the ICs), and these electronic components apply signal processing necessary to the transmission signals and the reception signals.

Between the inner case 112 and the outer case 102, a gap space is present, and a substrate 114 is disposed there. More specifically, the substrate 114 is fixed to the inner surface of the outer case 102 with a plurality of screws. On the under face of the substrate 114 (the face on the inner case 112 side), a temperature sensor 116 is provided. The temperature sensor 116 is configured of a thermistor. The temperature sensor 116 detects the ambient temperature T2.

Figure 5:
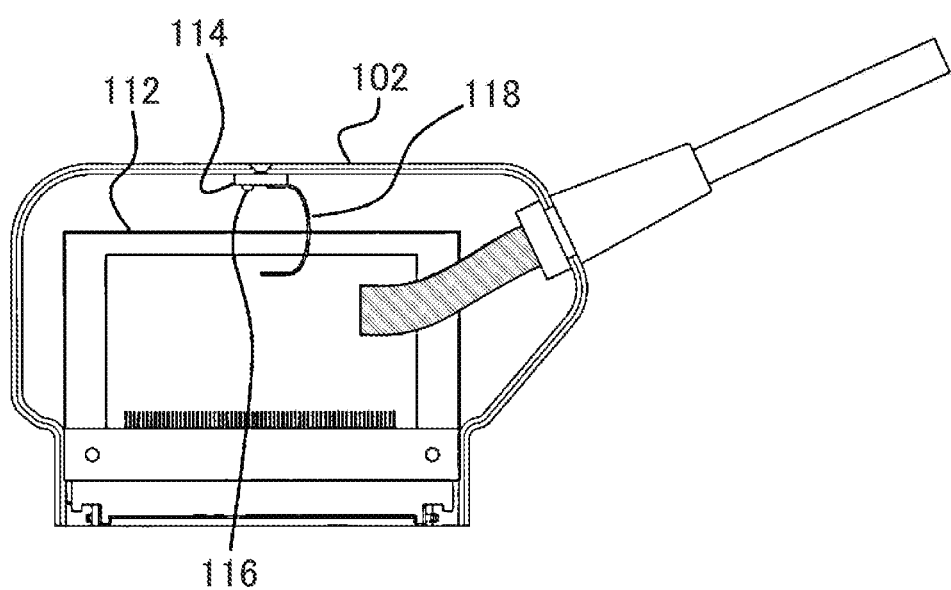
FIG. 5 is a diagram showing the inside of the connector.

FIG. 5 shows the inside of the connector. As described above, the substrate 114 is disposed between the outer case 102 and the inner case 112, and the temperature sensor 116 is disposed on the substrate 114. The substrate 114 is connected to a specific electronic circuit board with a signal line 118. since the temperature sensor 116 is disposed in the gap space, i.e., the temperature sensor 116 is disposed on the outer side of the inner case 112, even though heat is temporarily generated in the plurality of electronic circuit boards 110 (or even though heat from the apparatus main body reaches the plurality of electronic circuit boards 110), the temperature sensor 116 can be prevented from being affected by the heat, or even the influence of the heat can be reduced. since the temperature sensor is disposed in the inside of the outer case 102, the temperature sensor can be physically protected. However, the temperature sensor may be provided on another place (e.g. the main body).

Figure 6:
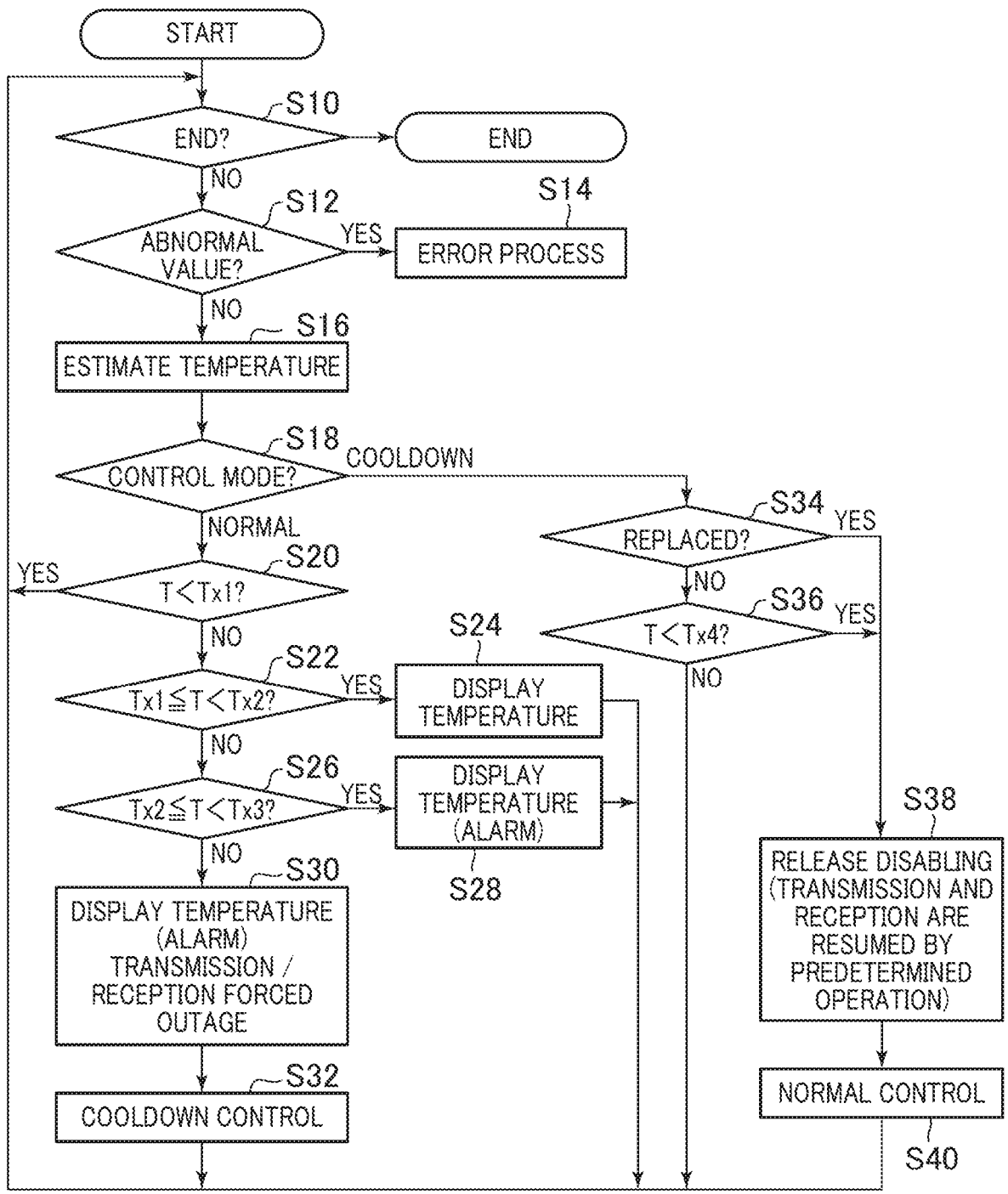
FIG. 6 is a flowchart showing an exemplary temperature management method.

FIG. 6 shows an exemplary temperature management method. In S10, it is determined whether this process is ended. In the case in which predetermined end conditions are satisfied, this process is ended. In S12, it is determined whether the internal temperature T1 and the ambient temperature T2 are in a normal range. In the case in which any of the temperatures corresponds to an abnormal value, the temperature sensor might fail, and hence an error process is executed in S14. An example of the error process includes displaying an alarm message, for example. In this case, heat generation suppression mode may be automatically set.

In S16, the temperature of the transmission-reception wavefront is estimated based on the transmission-reception conditions, the internal temperature, and the external temperature. As already described, in the embodiment, the estimation of the temperature TA according to the basic function and the estimation of the temperature TB according to the auxiliary function are concurrently executed, and any of two temperatures TA and TB is selected as the estimated temperature T. In S18, it is determined whether any of the normal control mode and the cooldown control mode is set.

In the case in which the normal control mode is set, in S20, it is determined whether the estimated temperature T is less than the first temperature Tx1 (e.g. 36 degrees). When the estimated temperature T is less than the first temperature Tx1, the steps after S10 are repeatedly executed. In S22, in the case in which it is determined that the estimated temperature is the first temperature Tx1 (e.g. 37 degrees) or more and less than the second temperature Tx2 (e.g. 40 degrees), in S24, the estimated temperature T is displayed in the normal display mode. In S26, in the case in which it is determined that the estimated temperature T is the second temperature Tx2 (e.g. 40 degrees) or more and less than the third temperature Tx3 (e.g. 43 degrees), in S28, the estimated temperature T is displayed in the highlighted display mode. At a present time, an alarm message is also displayed.

In the case in which it is determined as No in S26, i.e., in the case in which it is determined that the estimated temperature T is the third temperature Tx3 (e.g. 43 degrees) or more, similarly in S28, in S30, the temperature and any other parameter are displayed, and control that forcedly stops transmission and reception is executed. In S32, the cooldown control mode is set for cooling the transmission-reception wavefront.

In S18, in the case in which it is determined that the cooldown control mode is set as the control mode, the steps after S34 are executed. In S34, it is determined whether the ultrasound probe is replaced. In the case in which the ultrasound probe has been replaced, S38 is executed under certain conditions. In S36, in the case in which it is determined that the estimated temperature T reaches a temperature less than the fourth temperature Tx4 (e.g. 40 degrees), S38 is executed. In S38, the transmission-reception disabling state is released, i.e., transmission and reception can be resumed by performing a predetermined operation (freeze release operation). In S40, the normal control mode is set.

As described above, according to the embodiment, when the estimated temperature T reaches a certain temperature, transmission and reception are disabled, and after that, after the completion of cooldown is confirmed, resuming transmission and reception is permitted. In the previous stage of disabling transmission and reception, the estimated temperature is displayed, and necessary information is displayed, and hence the spontaneous cooldown action can be taken based on these pieces of information before reaching the forced outage of transmission and reception. After cooldown, transmission and reception are not automatically resumed, and hence an accidental temperature rise can be prevented.

In Equation (1) described above, i.e., in the basic function, the internal temperature T1 and the estimated temperature TA of the transmission-reception wavefront are in a linear relationship, and its slope is basically a constant value. The power consumptions Pic and Ptd and the ambient temperature T2 define the intercept of the basic function. On the other hand, in the rising period and the falling period caused by a sudden change in the state (i.e., the transition period), there are various temperature change modes depending on the time and content of a change in the state. Therefore, in Equation (2), i.e., the auxiliary function, the present temperature TB is estimated from the direction and the variation of the internal temperature change ΔT1 on the basis of the estimated temperature T in the past.

Figure 7:
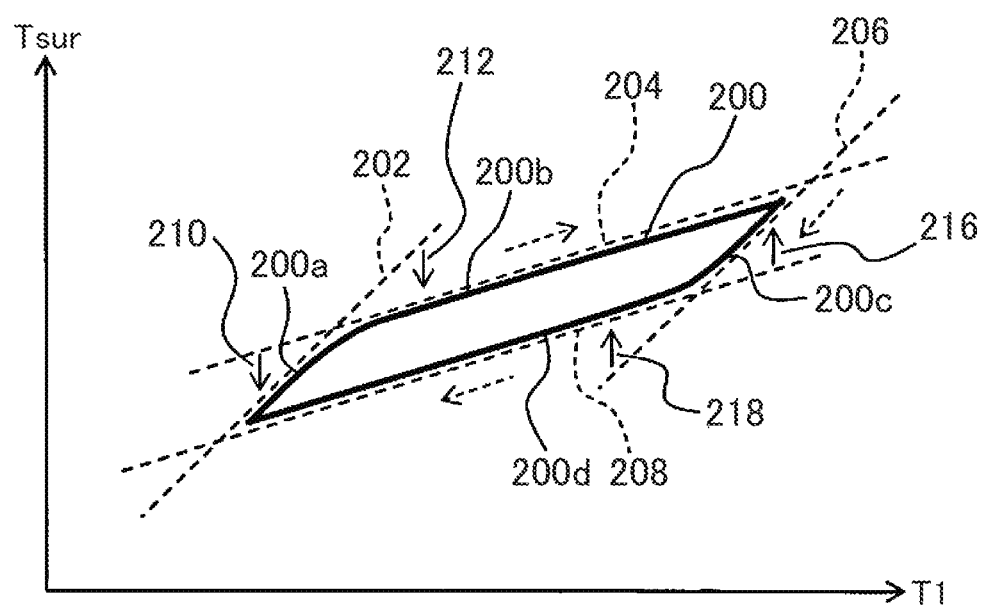
FIG. 7 is a diagram showing an exemplary temperature change including a temperature rise and a temperature drop after the rise.

FIG. 7 shows an exemplary temperature change including a temperature rise and a temperature drop after the rise. In the example shown in FIG. 7, a graph 200 is configured of a portion 200a corresponding to an initial rising period, a portion 200b corresponding to a normal period subsequent to the initial rising period, a portion 200c corresponding to a falling period caused by a change in the transmission-reception conditions (e.g. stop), and a portion 200d corresponding to a normal period subsequent to the falling period. The portion 200b and the portion 200d are in parallel with each other, but their offsets are different.

In the initial rising period, the portion 200a is approximated by the auxiliary function (see a reference sign 202), and in the normal period, the portion 200b is approximated by the basic function (see a reference sign 204). In the falling period, the portion 200c is approximated by the auxiliary function (see a reference sign 206), and in the normal period, the portion 200d is approximated by the basic function (see a reference sign 208). Of course, according to the power consumption of the ultrasonic transducer and the other parameters, more finer selection conditions can be provided.

Note that the form of the graph 200 greatly changes according to the types and structures of ultrasound probes. desirably, graphs are acquired for individual ultrasound probes, the tendencies are analyzed, and the selection conditions unique to each ultrasound probe are predetermined.

Since the form of the graph shown in FIG. 7, i.e., the hysteresis characteristics are varied depending on the ultrasound probe and the transmission-reception conditions, reference is desirably made to one or a plurality of parameters accordingly.

According to the embodiment, the estimation accuracy of the temperature of the transmission-reception wavefront 18A can be enhanced, compared with the case in which the temperature of the transmission-reception wavefront is estimated based on a single basic function. That is, in addition to the normal period in which the temperature can be estimated by the basic function, also in the transition period in which it is difficult to estimate the temperature by the basic equation, the temperature of the transmission-reception wavefront can be estimated at a certain accuracy. More specifically, the temperature of the surface-reception wavefront can be estimated also in consideration of the influence of the ambient temperature.

The invention claimed is:

1. An ultrasonic diagnostic apparatus comprising: a probe head including:
   an ultrasonic transducer,
   an electronic circuit electrically connected to the ultrasonic transducer,
   an internal temperature sensor configured to detect an internal temperature, and
   a protective layer having a surface being a transmission-reception wavefront;
   a processor configured to estimate a temperature of the transmission-reception wavefront based on a transmission-reception condition and the internal temperature, the processor being configured to estimate a temperature of the transmission-reception wavefront based on a function group including a basic function that is a temperature estimation function for a first period and an auxiliary function that is a temperature estimation function for a second period in which the basic function is not held, wherein the second period is a temperature change period in which changing of temperature occurs faster than a temperature change in the first period, wherein (i) a first slope of temperature in a first region and a second region of the first period is substantially constant, the temperature in the first region being offset from that in the second region, and (ii) a second slope of temperature in a first region and a second region of the second period is substantially constant, the temperature in the first region being offset from that in the second region; and
   an ambient temperature sensor configured to detect an ambient temperature, wherein the processor is configured to estimate the temperature of the transmission-reception wavefront further based on the ambient temperature,
   wherein the basic function temperature of the transmission-reception wavefront is a linear expression that estimates the temperature of the transmission-reception wavefront based on power consumption that is based on the transmission-reception condition, the internal temperature, and the ambient temperature, wherein the linear expression is provided by $$TA = \alpha \times T1 + C1 + C2 + C3,$$

wherein TA is the temperature of the basic function, a is a slope coefficient, T1 is the internal temperature, (C1+C2+C3) defines an intercept, C1 is determined by the multiplication of the power consumption by a predetermined coefficient, and C2 is determined by the multiplication of the ambient temperature by a predetermined coefficient, wherein the auxiliary function is a recurrence formula that estimates the temperature of the transmission-reception wavefront based on a previously estimated temperature and a difference between the internal temperature detected at a present time and the previously detected internal temperature, the recurrence formula provided by $$TB = Tpre + \beta \times \Delta T1,$$

wherein TB is a temperature of the auxiliary function, Tpre is the previously estimated temperature, $\Delta T1$ is the difference between the internal temperature detected at a present time and the previously detected internal temperature, and p is a slope coefficient, wherein the processor includes a first processor configured to perform the basic function and a second processor configured to perform the auxiliary function.

2. The apparatus according to claim 1, further comprising a selector circuit, the selector circuit being configured to:
   compute a first temperature according to the basic function and a second temperature according to the auxiliary function in a parallel manner,
   select any of the first temperature or the second temperature, and
   output the selected temperature as an estimated temperature.

3. The apparatus according to claim 2,
   wherein the selector circuit is configured to select any of the first temperature or the second temperature based on the internal temperature, and on a comparison result of the first temperature with the second temperature.

4. A temperature management method comprising:
   estimating a temperature of a transmission-reception wavefront being a surface of a protective layer of a probe head, the probe head having an ultrasonic transducer, an electronic circuit, and the protective layer; and
   controlling transmission and reception by the estimated temperature, wherein the estimating includes:

computing a temperature of the transmission-reception wavefront as a first temperature based on a basic function that is a temperature estimation function in a first period, computing a temperature of the transmission-reception wavefront as a second temperature in a second period based on an auxiliary function that is a temperature estimation function for the second period, and the second period is a temperature change period in which changing in temperature occurs faster than a temperature change in the first period, wherein (i) a first slope of temperature in a first region and a second region of the first period is substantially constant, the temperature in the first region being offset from that in the second region, and (ii) a second slope of temperature in a first region and a second region of the second period is substantially constant, the temperature in the first region being offset from that in the second region; and selecting the first temperature or the second temperature as an estimated temperature, wherein the basic function temperature of the transmission-reception wavefront is a linear expression that estimates the temperature of the transmission-reception wavefront based on power consumption that is based on the transmission-reception condition, an internal temperature, and an ambient temperature, wherein the linear expression is provided by $$TA = \alpha \times T1 + C1 + C2 + C3,$$

wherein TA is the temperature of the basic function, a is a slope coefficient, T1 is the internal temperature, (C1+C2+C3) defines an intercept, C1 is determined by the multiplication of the power consumption by a predetermined coefficient, and C2 is determined by the multiplication of the ambient temperature by a predetermined coefficient, wherein the auxiliary function is a recurrence formula that estimates the temperature of the transmission-reception wavefront based on a previously estimated temperature and a difference between the internal temperature detected at a present time and the previously detected internal temperature, the recurrence formula provided by $$TB = Tpre + \beta \times \Delta T1,$$

wherein TB is a temperature of the auxiliary function, Tpre is the previously estimated temperature, $\Delta Ti$ is the difference between the internal temperature detected at a present time and the previously detected internal temperature, and p is a slope coefficient, wherein the basic function is performed by a first processor and the auxiliary function is performed by a second processor.

5. The ultrasonic diagnostic apparatus of claim 1, wherein the processor is further configured to estimate the temperature of the transmission-reception wavefront based on a diagnostic mode.

6. The ultrasonic diagnostic apparatus of claim 5, wherein the processor is further configured to estimate the power consumption based on the transmission-reception condition, the internal temperature, the ambient temperature and the diagnostic mode.

7. The ultrasonic diagnostic apparatus of claim 5, wherein the processor is configured to communicate with a display screen to display the estimated temperature.

\* \* \* \* \*